United States Patent [19]

Greco

[11] 4,275,246

[45] Jun. 23, 1981

[54] SEPARATION OF PHENOLS

[75] Inventor: Nicholas P. Greco, Pittsburgh, Pa.

[73] Assignee: Koppers Company, Inc., Pittsburgh, Pa.

[21] Appl. No.: 53,968

[22] Filed: Jul. 2, 1979

[51] Int. Cl.³ .................... C07C 37/68; C07C 37/70
[52] U.S. Cl. .................................. 568/750; 568/751; 568/752
[58] Field of Search .................. 568/750, 751, 752

[56] References Cited

U.S. PATENT DOCUMENTS

| | | | |
|---|---|---|---|
| 1,445,668 | 2/1923 | Derby et al. | 568/750 |
| 1,980,384 | 11/1934 | Comte | 568/750 |
| 3,517,072 | 6/1970 | Moronie et al. | 568/750 |
| 4,001,341 | 1/1977 | Welch et al. | 568/750 |

FOREIGN PATENT DOCUMENTS

| | | | |
|---|---|---|---|
| 33-120516 | 7/1958 | Japan | 568/750 |
| 51-98228 | 8/1976 | Japan | 568/751 |
| 268433 | 8/1970 | U.S.S.R. | 568/751 |

*Primary Examiner*—Werren B. Lone
*Attorney, Agent, or Firm*—Donald M. MacKay

[57] ABSTRACT

Effluent containing cresols such as are contained in Lurgi tar acids are separated by preferentially treating the cresols with an aqueous alkali metal carbonate or bicarbonate at elevated temperature for a time sufficient to form the alkali metal salt of at least part of the cresols, but not so long as to form any appreciable alkali metal salt of 2,6-xylenol or o-ethylphenol. The water soluble alkali metal salts of cresols are then separated from the water insoluble phenols and said salts acidified to "spring" the cresols and the water insoluble cresols separated from the aqueous solution.

9 Claims, No Drawings

SEPARATION OF PHENOLS

BACKGROUND OF THE INVENTION

In the Lurgi process where coal is gasified, there are tar oil by-products comprising o-cresol, p-cresol, m-cresol, o-ethylphenol, 2,6-xylenol, 2,4-xylenol, and 3,5-xylenol. While the cresols are valuable, the tar acids are discarded because of the difficulty of separating the cresols from the o-ethylphenol and 2,6-xylenol. Since they have the same approximate boiling point they can't be separated by distillation.

Similarly, the oil industry extracts phenolics with caustic but is not able to separate the phenols from one another.

DESCRIPTION OF THE INVENTION

It has been discovered that phenols, such as are contained in industrial effluent and discarded, can be recovered. More particularly, it has been found that cresols can be separated from o-ethylphenol and 2,6-xylenol, which is not presently commercially practical.

In accordance with the invention, tar acids or any solution or effluent containing the above phenols is treated with an aqueous alkali metal carbonate or bicarbonate at high temperature for a time sufficient to preferentially form the alkali metal salt of at least part of the cresol, and render it soluble in the aqueous solution, but not so long as to form any appreciable amount of alkali metal salt of 2,6-xylenol, or o-ethylphenol. Samples can be analyzed periodically during the reaction to determine the composition. At least 50 percent of the cresols can be converted to the alkali metal salt without any appreciable formation of 2,6-xylenol or o-ethylphenol salts, but generally 90 percent or more of the cresols can be converted without any appreciable by-product salts.

Although the alkali metal carbonate employed to treat the cresols can be potassium carbonate, potassium bicarbonate, sodium carbonate and sodium bicarbonate, the sodium salts, and particularly sodium bicarbonate, is preferred. An excess of from 19 to 30 percent above stoichiometric is preferably employed as it helps to separate the unreacted tar acids from the acids in solution by decantation or extraction.

The reaction can be conveniently conducted employing a reaction pot fitted with a heating mantle and a water-cooled condenser. The phenols, water and alkali metal carbonate (hereinafter referred to as sodium bicarbonate for convenience) are charged to the reactor. The reaction is preferably conducted under pressure in order to obtain rapid reaction. Reaction can be conveniently obtained at a temperature between about 100° C. and 197° C. and at a pressure between about 0 and about 180 psig. For best results, the carbon dioxide formed is removed by means of a purge of air or inert gas such as nitrogen. A dip tube can be employed to pass the purging gas under the reactants. It is necessary to remove the carbon dioxide or reaction will not take place, as the carbon dioxide will react with caustic soda to form sodium bicarbonate according to the following reversible reaction.

$$NaHCO_3 \rightleftharpoons NaOH + CO_2$$

With the purge of carbon dioxide, the caustic soda is reacted with the cresols. The carbon dioxide can be collected or passed to a second reactor to acidify the sodium salt of the cresols (infra). The water is not lost in the form of steam because it is condensed in the jacketed water-cooled condenser and returned to the reactor.

Before the evolution of carbon dioxide subsides and while some free cresol remains, as indicated by G.C. analysis, the reaction is terminated and the water insoluble phenols can be separated from the water soluble sodium cresol salts and the latter sprung with carbon dioxide to form the free cresols and sodium bicarbonate. The sodium bicarbonate can then be used to treat fresh tar acids or other solution containing phenols.

The cresol salts can be sprung with carbon dioxide or strong acids such as hydrochloric or sulfuric. Carbon dioxide is preferred, however, and can be further used to regenerate the alkali metal carbonate.

Enough $CO_2$ is used under pressure until it is no longer absorbed or, if the reaction is not conducted under pressure, enough is used to obtain a solution with an acid pH.

The water soluble alkali metal cresol salts may be separated from the water insoluble phenols, and the water insoluble cresols from the aqueous alkali metal carbonate by decanting, steam distillation or solvent extraction.

The following examples will serve to illustrate the invention. All parts and percentages in said examples and elsewhere in the specification and claims are by weight unless otherwise specified.

EXAMPLE I

A reactor as described (supra) was charged with 50 g of Lurgi tar (containing tar acids with a boiling point range of 190° C.–230° C.), 84 g of sodium bicarbonate and 350 ml. of water. Nitrogen under 175 psi was pressured into the reactor above the liquid level to purge $CO_2$ and the reactor was heated at 196° C. for 1 hour and 50 minutes.

The water insolubles were extracted with ether to produce 27 g (54%) of phenols of the distribution shown in the table. The aqueous solution containing the sodium salt of the remaining tar acids (solubles) was acidified with $CO_2$ until a sample of the solution was acidic to "spring" the acids and the acids recovered from the non-aqueous phase by ether extraction. The yield of solubles (extract 2) was 23 g (46%) with the following distribution:

| % Insolubles | Tar Acids | % Solubles |
|---|---|---|
| 57.1 | cresols | 91.3 |
| 1.2 | o-ethylphenol | 0.1 |
| 5.6 | 2,6-xylenol | 0.45 |
| 18.1 | 2,4- & 2,5-xylenol | 1.5 |
| 15.0 | p-ethylphenol | 6.4 |
| 2.8 | 2,3- & 3,5-xylenol | 0.1 |

From the analysis, it can be seen that the difficulty to separate o-ethylphenol and 2,6-xylenol were primarily retained in the insoluble fraction of the first extraction so that the cresols recovered from the soluble second extraction are relatively free of impurities.

EXAMPLE II

Employing an apparatus as described, the reactor was charged with 86 g of tar acids (Ferro Corp. Productol Cresylic Acid M/p88) which had the following composition:

cresols: 91.0%
2,6- and ortho-ethylphenol: 6.3%

2,4- and other xylenols: 2.7%

In addition to the tar acids, the reactor was charged with 70 g of water and 84 g of sodium bicarbonate and the mixture heated at 194° C. under 170 psi of nitrogen pressure. Carbon dioxide started to evolve at 105° C. In 1.25 hours the reaction was arbitrarily stopped to analyze the mixture by G.C., the reaction product allowed to cool to room temperature (30° C.), and then the non-aqueous phase system extracted with ether to remove the tar acids not in solution, which was 31 g or 36 percent of the tar acids charged. The distribution for these insolubles is shown in the table below. The aqueous solution containing the sodium salt of the remaining tar acids was acidified with $CO_2$ until a sample of the solution was acidic to "spring" the acids and the acids recovered from the non-aqueous phase by ether extraction to yield 55 g or 64 percent of the tar acids charged. The composition of the tar acid water insolubles (extract 1) and water solubles (extract 2) in the sodium bicarbonate solution were as follows:

| % Insolubles | Tar Acids | % Solubles |
|---|---|---|
| 83.2 | cresols | 98.9 |
| 0.9 | o-ethylphenol | 0.1 |
| 13. | 2,6-xylenol | 0.8 |
| 0.3 | other xylenols | 0.3 |

Thus, it can be seen from the soluble fraction that the cresols are recovered substantially free of any impurities.

While the invention has been described with the preferred embodiments, numerous obvious variations will occur to those of ordinary skill which will lie within the true scope of this invention. Accordingly, the invention is to be limited only by the appended claims.

What is claimed:

1. A method for separating cresol from o-ethylphenol and/or 2,6-xylenol comprising treating the aforesaid phenols with an aqueous alkali metal carbonate or bicarbonate at elevated temperature in an amount and for a time sufficient to preferentially form the alkali metal salt of at least 50% of the cresol, but not so long as to form any appreciable amount of alkali metal salt of 2,6-xylenol or o-ethylphenol, separating the water soluble alkali metal salt of cresol from the water insoluble phenols, acidifying said alkali metal salt to "spring" the cresol and separating the cresol from the aqueous solution.

2. The process of claim 1 wherein the cresol is a mixture of ortho, meta- and para-cresols and the phenols are contained in a mixture of coal tar acids.

3. The process of claim 1 wherein the alkali metal is sodium or potassium.

4. The process of claim 1 wherein the alkali metal is sodium.

5. The process of claim 1 wherein the phenols are treated with the alkali metal carbonate or bicarbonate until the alkali metal salt of about 90 percent of the cresol is formed.

6. The process of claim 1 wherein the elevated temperature is between about 100° C. and about 197° C.

7. The process of claim 1 wherein the alkali metal carbonate or bicarbonate are contacted with the phenols at superatmospheric pressure.

8. The process of claim 1 wherein $CO_2$ is used to acidify the alkali metal cresol salts.

9. The process of claim 1 wherein the phenols are treated with the alkali metal carbonate in the presence of a gas to purge the carbon dioxide by-product.

* * * * *